(12) United States Patent
Chinavare

(10) Patent No.: US 7,546,775 B2
(45) Date of Patent: Jun. 16, 2009

(54) BEND TOOL

(75) Inventor: Jason Chinavare, Minnetonka, MN (US)

(73) Assignee: Bose Corporation, Feamingham, MA (US)

( * ) Notice: Subject to any disclaimer, the term of this patent is extended or adjusted under 35 U.S.C. 154(b) by 37 days.

(21) Appl. No.: 11/757,772

(22) Filed: Jun. 4, 2007

(65) Prior Publication Data

US 2008/0295606 A1    Dec. 4, 2008

(51) Int. Cl.
*G01L 1/22*    (2006.01)
(52) U.S. Cl. .......................... 73/849; 73/862
(58) Field of Classification Search ............ 73/788, 73/830, 849, 852
See application file for complete search history.

(56) References Cited

U.S. PATENT DOCUMENTS

| | | | |
|---|---|---|---|
| 2,787,157 A | | 4/1957 | Angevine |
| 4,898,037 A | * | 2/1990 | Allen et al. .................. 73/866 |
| 5,503,024 A | | 4/1996 | Bechtel et al. |
| 5,592,875 A | * | 1/1997 | Moschel ...................... 100/99 |
| 5,892,157 A | | 4/1999 | Syré |
| 6,055,867 A | * | 5/2000 | Dunne et al. .................. 73/849 |
| 6,381,546 B1 | * | 4/2002 | Starostovic .................. 702/36 |
| 6,505,129 B2 | * | 1/2003 | Starostovic et al. ........... 702/36 |
| 6,663,617 B1 | | 12/2003 | Vito et al. |
| 6,810,751 B2 | * | 11/2004 | Moreno et al. ................. 73/849 |
| 7,201,064 B2 | * | 4/2007 | Doak et al. ................... 73/849 |
| 2004/0016301 A1 | | 1/2004 | Moreno et al. |
| 2007/0068274 A1 | | 3/2007 | Olson et al. |

FOREIGN PATENT DOCUMENTS

| | | |
|---|---|---|
| DE | 196 37 808 | 12/1997 |
| FR | 2793033 | 11/2000 |
| WO | WO00/66996 | 11/2000 |

OTHER PUBLICATIONS

International Search Report and Written Opinion in Application No. PCT/US2008/065747, dated Jul. 31, 2008.

* cited by examiner

*Primary Examiner*—Lisa M Caputo
*Assistant Examiner*—Freddie Kirkland, III

(57) ABSTRACT

A tool for multi-axis mechanical testing of medical implant devices includes a plurality of pins arranged to form a contacting surface with a sample holder. The pins maintain rolling contact with the sample holder during a bending phase of a fatigue cycle and reduce the effects of friction and localized differential strain on the sample holder.

20 Claims, 9 Drawing Sheets

BEND TOOL

BACKGROUND

The present invention relates to mechanical testing of medical implant devices.

SUMMARY

A tool for multi-axis mechanical testing of medical implant devices includes a plurality of pins arranged to form a contacting surface with a sample holder. The pins maintain rolling contact with the sample holder during a bending phase of a fatigue cycle and reduce the effects of friction and localized differential strain on the sample holder.

One embodiment of the present invention is directed to a bend tool comprising: a first end cap; a second end cap; and an array of pins, each pin in the array of pins having a first end rotatably supported by the first end cap and a second end rotatably supported by the second end cap. In one aspect, at least one pin in the pin array supports a rotatable sheath. In one aspect, each pin of the pin array supports a rotatable sheath. In one aspect, the rotatable sheath slides along a longitudinal axis of the pin between the first and second end cap. In one aspect, the rotatable sheath is characterized by a length, the sheath length determined by a position of the pin in the pin array. In one aspect, the array of pins projected onto the first end cap approximates a desired bend curve. In one aspect, the desired bend curve is characterized by a single radius of curvature. In one aspect, the desired bend curve is characterized by a plurality of radii of curvature. In one aspect, the desired bend curve simulates an expected in-use bend curve. In another aspect, a fatigue testing device for a stent comprises the above-described bend tool. In another aspect, the fatigue testing device further comprises an upper strain relief tool, the upper strain relief tool having a first relief end cap, a second relief end cap, and an array of relief pins, each relief pin in the array of relief pins having a first end rotatably supported by the first relief end cap and a second end rotatably supported by the second relief end cap.

Another embodiment of the present invention is directed to a bend tool comprising: a first end cap; a second end cap; an array of pins, each pin in the array of pins having a first end held by the first end cap and a second end held by the second end cap, each pin in the array supporting a rotatably sheath. In an aspect, the rotatable sheath is sized to allow rotation of the sheath around a longitudinal axis of the supporting pin and sliding of the sheath along the longitudinal axis of the supporting pin. In an aspect, the rotatable sheath is characterized by a length, the sheath length determined by a position of the pin in the pin array. In an aspect, the pins in the array of pins are arranged along a desired bend curve, the desired bend curve simulating an expected in-use bend of a stent.

DETAILED DESCRIPTION

Although more commonly known for their use in coronary arteries, stents may be implanted in peripheral arteries or other tubular structures within an organism. Peripheral arteries include, for example, renal arteries, carotid arteries, and femoral-popliteal arteries. Peripheral arteries generally experience greater bending, twisting, and stretching motions relative to coronary arteries and it is expected that stents implanted in a peripheral artery will likely experience greater stresses and strains relative to a coronary stent.

Figure 1A:
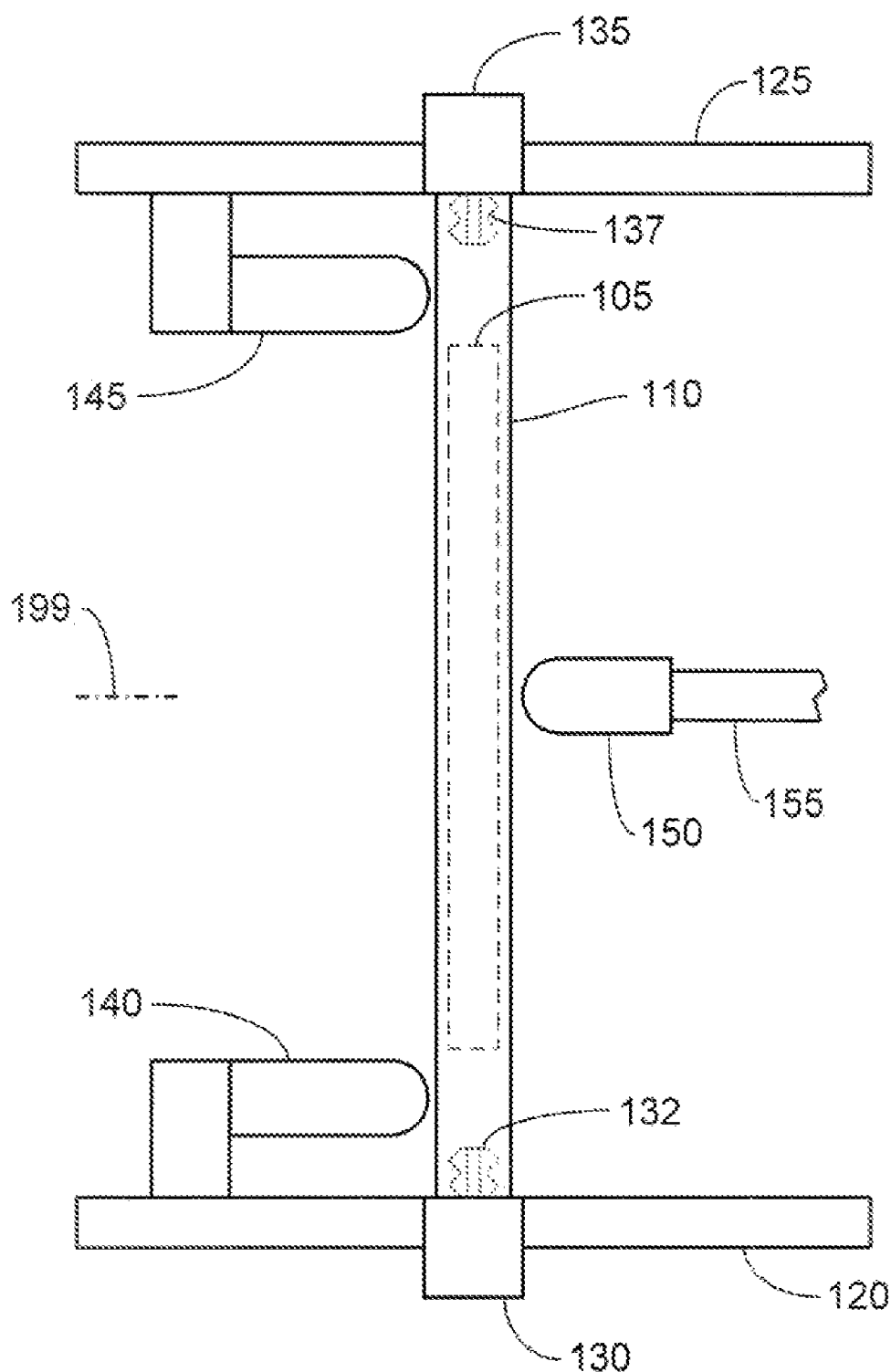
FIG. 1a shows a stent fatigue system.

FIG. 1a illustrates a configuration used to fatigue test a stent such as, for example, a peripheral artery stent. In FIG. 1a, stent 105 is held within a sample holder 110. The sample holder 110 is preferably an elastic material such as, for example, latex, silicone, and thermoplastic elastomers. The sample holder 110 preferably acts as the tubular structure during the fatigue test and is sized to accommodate the size and length of the stent being tested. The sample holder 110 is supported at one end by a grip 130, which is supported by a fixed stage 120. The other end of the sample holder is supported by a grip 135 mounted on a vertically movable stage 125. In some embodiments, grips 130 and 135 are rotatably supported by stages 120 and 125, respectively, to simulate torsion of the sample. Grips 130, 135 may be an inner barb fitting 132, 137 inserted into the end of the sample holder and a clamp (hot shown) around the outer circumference of the sample holder and over the inner barb fitting. The inner barb fittings may be configured to allow fluid flow through the sample holder and stent to simulate in-use conditions such as pulsatile flow within an artery. Similarly, grips 130, 135 may provide a fluid passage between the sample holder and a fluid circuit external to the sample holder.

Upper strain relief tool 145 and lower strain relief tool 140 provide lateral support for the sample holder during a portion of the bending cycle and form the two outer support points of a three-point bend test configuration. The third point of the three-point bend configuration is provided by a bend tool 150. Bend tool 150 is mechanically supported by support 155, which may be a part of a mechanical linkage (not shown) driven by an actuator (not shown). In some embodiments, the mechanical linkage and actuator work together to laterally displace the bend tool while keeping the bend tool centered between the upper and lower strain relief tools, indicated in FIG. 1a by line 199. In other embodiments, a simple straight support may be used to link the bend tool to the actuator mounted at a fixed elevation and both the upper and lower stages are displaced vertically to keep the bend tool centered between the upper and lower strain relief tools.

Figure 1B:
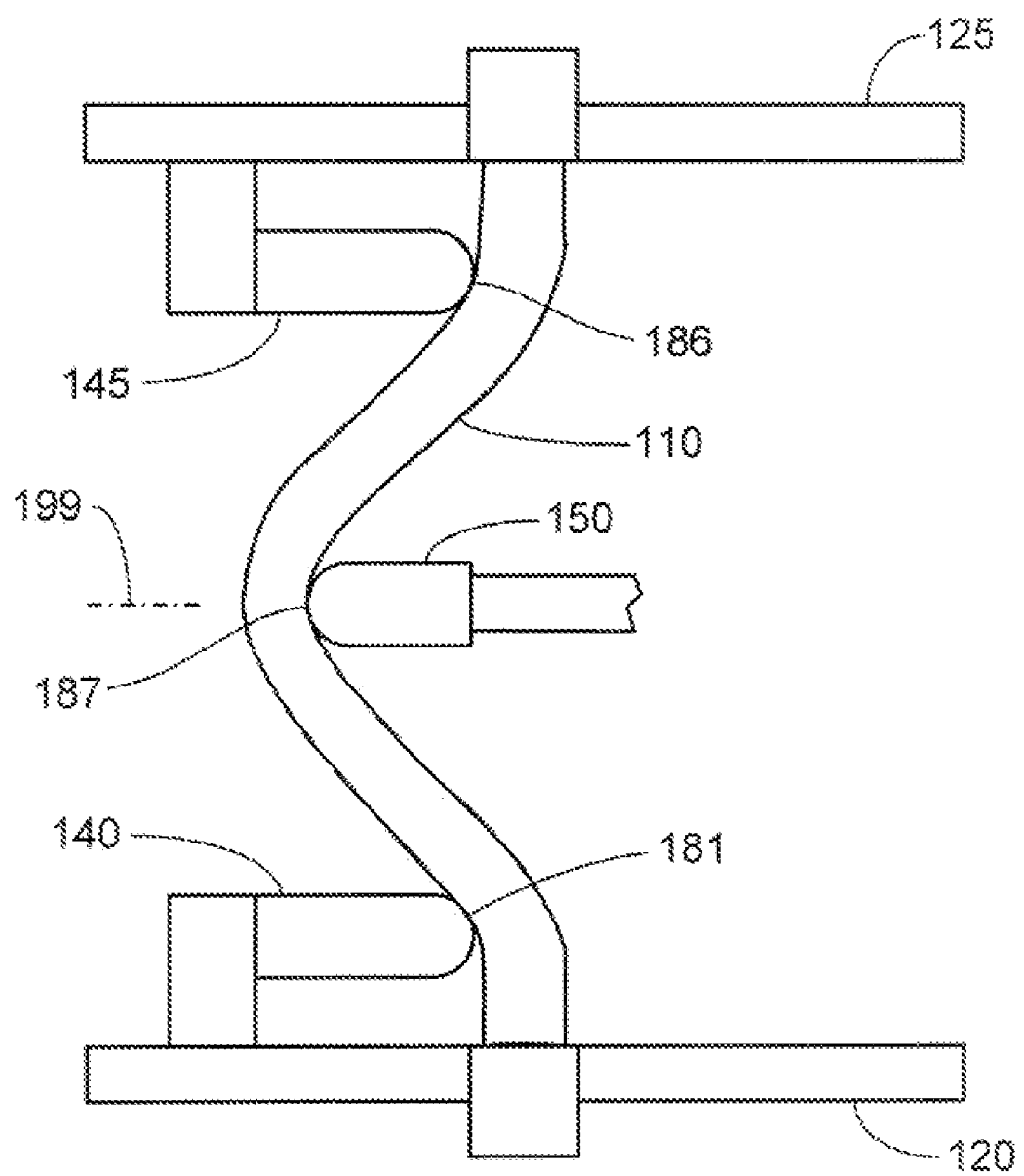
FIG. 1b shows the fatigue system of FIG. 1a at another phase of the fatigue cycle.

FIG. 1b illustrates a configuration at another instant of the fatigue cycle where bend tool 150 is in contact with the sample holder 110 and has been displaced laterally to bend the sample holder 110 and the stent held within the sample holder 110. FIG. 1b shows the upper stage 125 displaced vertically such that the longitudinal, or axial, strain on the stent is constant. The vertical displacement of the upper stage 125 may be controlled independently from the lateral displacement of the bend tool 150 thereby enabling independent control of both the axial strain profile and bending strain profile during a fatigue cycle.

Stents are typically fatigue tested to simulate 10 years of normal use and, depending on the application, could mean fatigue testing a stent for up to four hundred million bending cycles. During such testing, the inventor discovered failures of the sample holder that prematurely terminated the fatigue test before the stent failed or before the test reached the desired number of fatigue cycles. Failures at locations 187, 181, 186 were in or near areas where the sample holder contacted the bend tool or strain relief tools. Without being limiting, the inventor believes these failures to be attributed to friction and shear forces exerted on the sample holder by rigid bend and relief tools.

Figure 2:
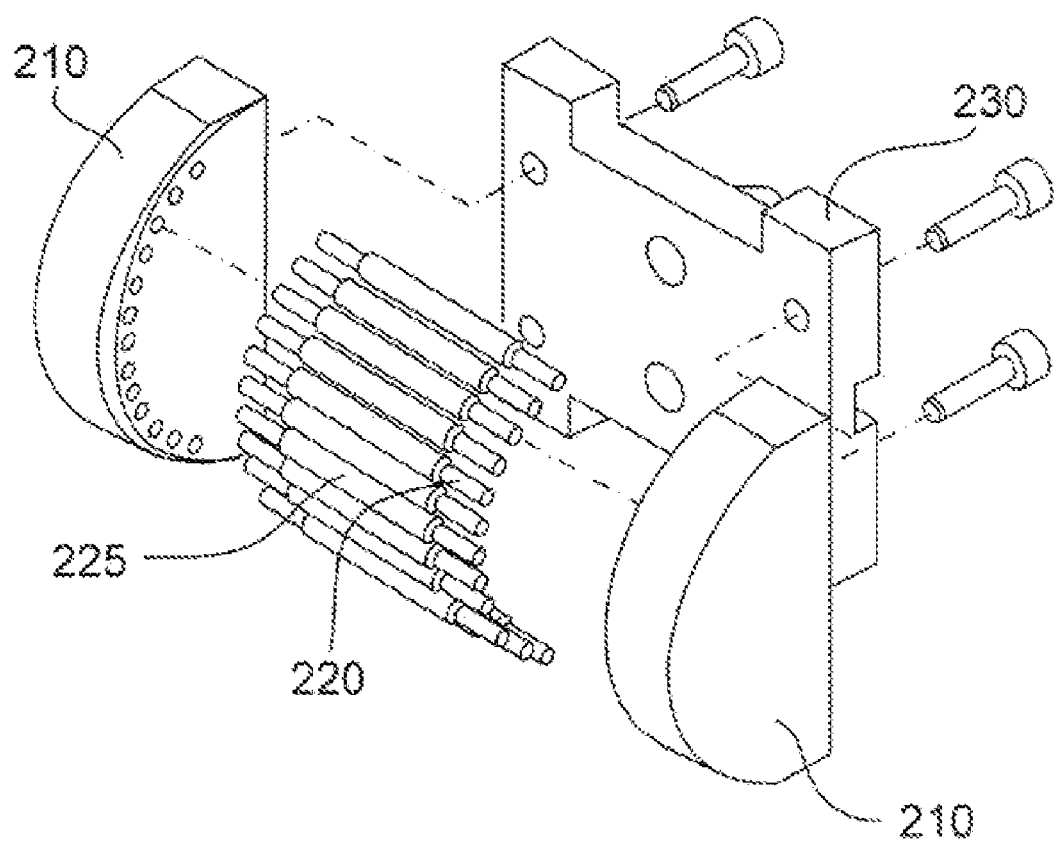
FIG. 2 is an exploded view of a bend tool.

FIG. 2 is an exploded view of a bend tool. In FIG. 2, an array of pins is held in place by end caps 210. The end caps 210 are supported by a mounting bracket 230. Each pin 220 in the pin array can freely rotate around the pin's longitudinal axis. In some embodiments, an over-sized sleeve or sheath 225 covers a portion of the pin 220 and can freely slide axially and circumferentially relative to the pin 220.

Figure 3:
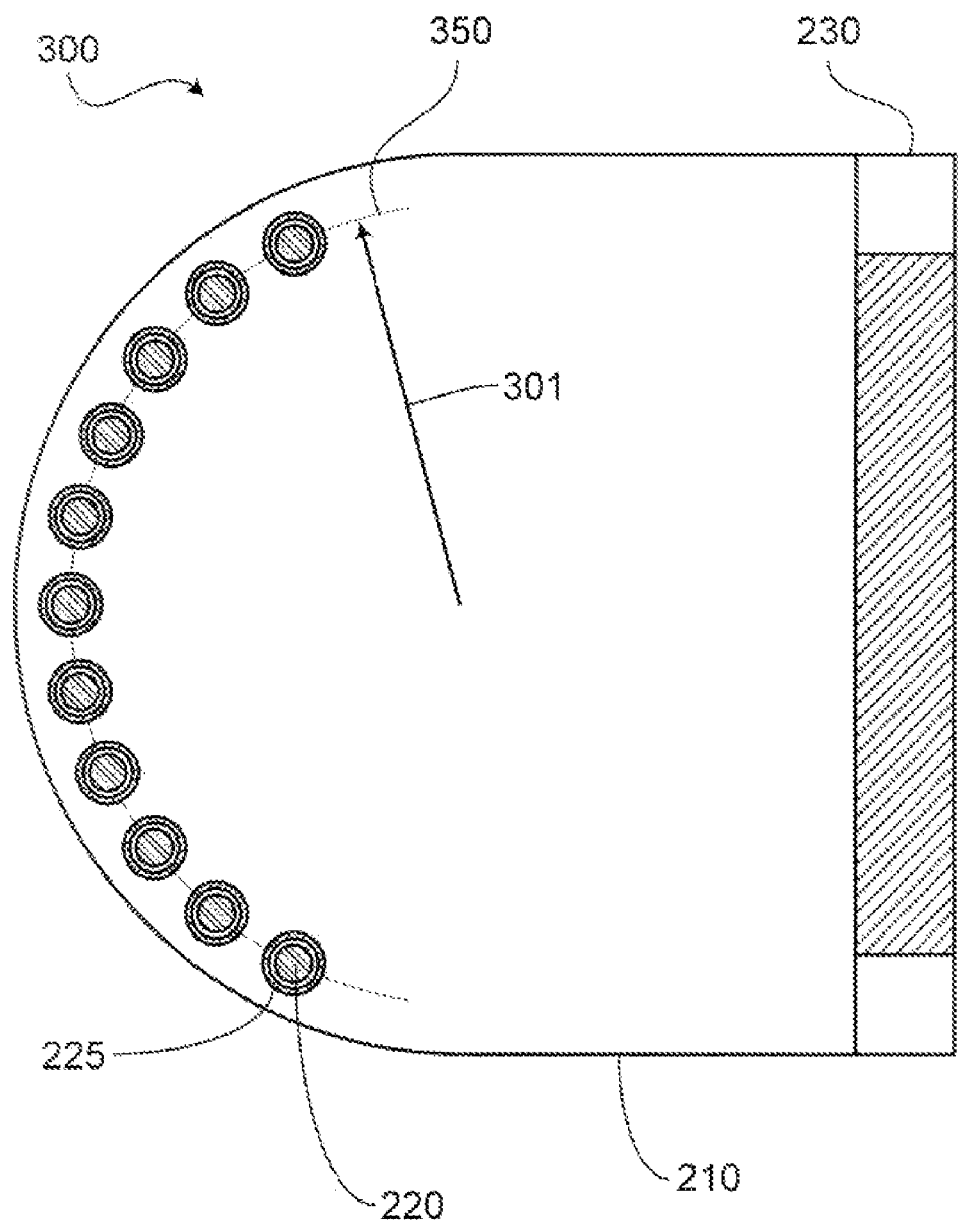
FIG. 3 is a sectional side view of the bend tool of FIG. 2.

FIG. 3 is a sectional side view of the bend tool shown in FIG. 2. In FIG. 3, like reference numbers refer to like structures. The pins in the pin array illustrated in FIG. 3 are arranged such that the intersection of each pin's longitudinal axis with the plane of the drawing in FIG. 3 is on a curve 350 having a common radius of curvature 301. The radius of curvature 301 preferably simulates the curvature expected under in-use conditions of the stent after adjustment is made for the pin radius, the optional sheath thickness, and the sample holder thickness. Curve 350 preferably approximates the expected bending curve of the stent during use and may include compound curves have several radii of curvature or a continuously varying radii of curvature.

End cap 210 preferably comprises a low friction material such as, for example, acetal resin engineering plastic available as Delrin® acetal resin from E.I. Du Pont de Nemours and Company of Wilmington, Del. A blind hole for each pin 220 is formed in the end cap 210 and one end of the pin is inserted in the blind hole. The blind hole is sized such that the pin 220 freely rotates within the blind hole.

Pin 220 preferably comprises a strong and stiff material such as, for example, stainless steel that resists deformation or failure during the repeated fatigue cycle. The diameter of each pin may be selected based on the pin material properties and the sample holder material properties. For example, a smaller diameter may be selected to reduce the contact area of the pin and sample holder but a larger diameter may be desired to reduce the bending deformation of the pin when the bend tool is pushed against the sample holder. Pin spacing may be selected based on factors such as, for example, pin diameter, bend curvature, and sheathing. Complicated bend curves or small pin diameters may favor small pin spacing whereas large pin diameters and pin sheathing may favor large pin spacing.

A sheath or sleeve 225 may be fitted over one or more pins in the pin array. For example, FIGS. 2 and 3 illustrate an embodiment where a sheath 225 is fitted over each pin in the pin array. The sheath 225 is sized such that the sheath can freely rotate around the pin's longitudinal axis and preferably comprises a material having a low coefficient of friction such as, for example, polytetrafluoroethylene, high-density polyethylene, and nylon. Other embodiments may include substituting the sheath with a low-friction thin film deposited onto each pin. Examples of low—friction thin films include diamond-like carbon thin films form using a chemical vapor deposition process. Other embodiments may eliminate the sheath such that the pins in the bend tool directly contact the sample holder. These embodiments enable closer pin spacing and may be favored when the desired bending curve is complex and has several radii of curvature characterizing the desired bending curve.

In some embodiments, a sheath or sleeve may be fitted over one or more pins in a pin array where the pins in the pin array are held in place by the end caps and do not rotate. The sheath, however, is sized such that each sheath can rotate around its corresponding pin axis and can slide in axially between the end caps as the sheath contacts the sample holder during the bending portion of the fatigue cycle.

Figure 4:
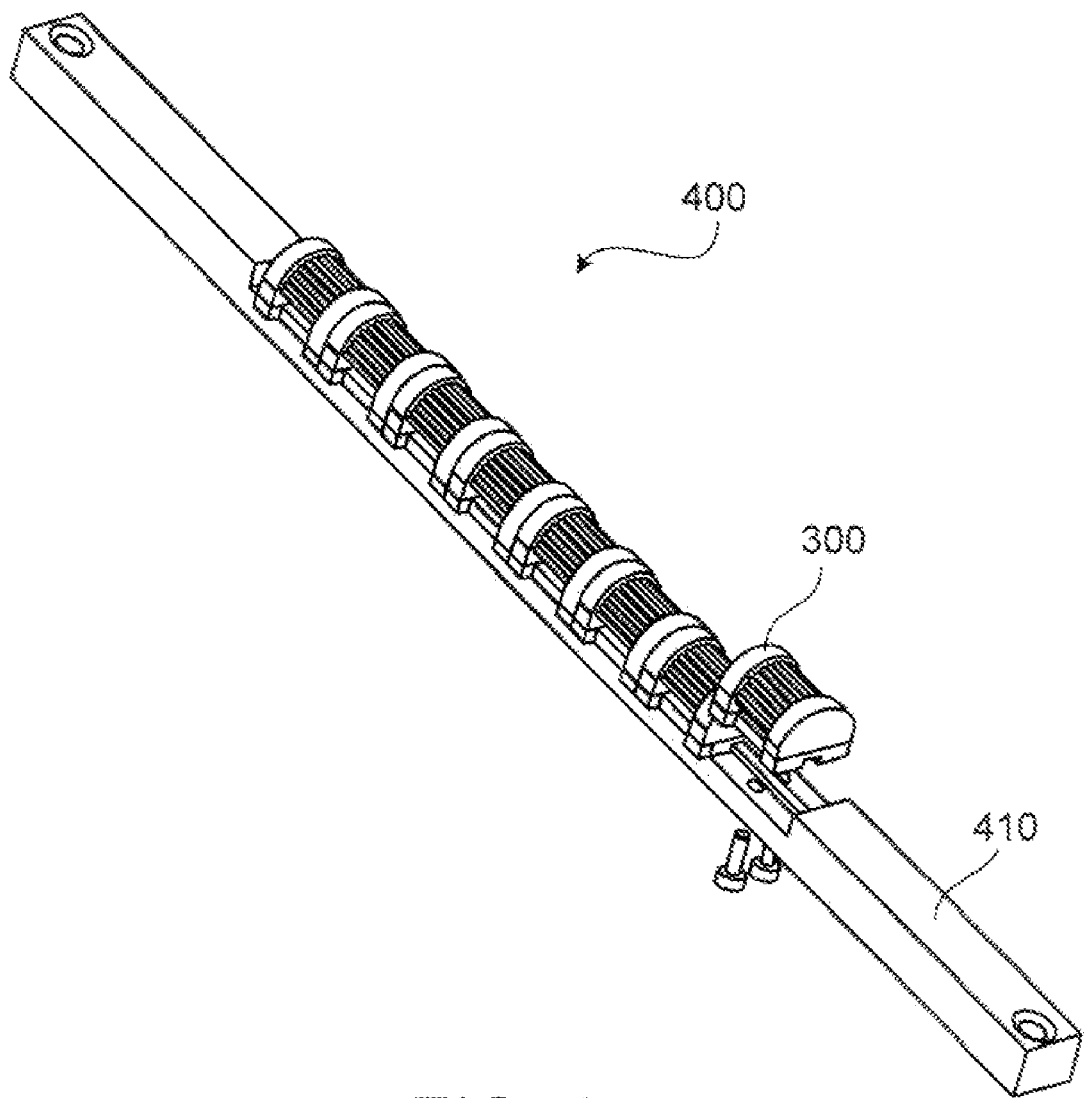
FIG. 4 is a perspective view of a bend tool assembly.

FIG. 4 is a partially exploded perspective view of a bend tool assembly 400. The bend tool assembly 400 includes at least one bend tool 300 mounted on an assembly bracket 410. The assembly bracket 410 may be mounted to one or more actuators through a mechanical linkage such that the one or more actuators control the lateral displacement of each bend tool. The bend fool assembly 400 enables simultaneous testing of more than one sample thereby reducing the time required for testing multiple samples.

Figure 5:
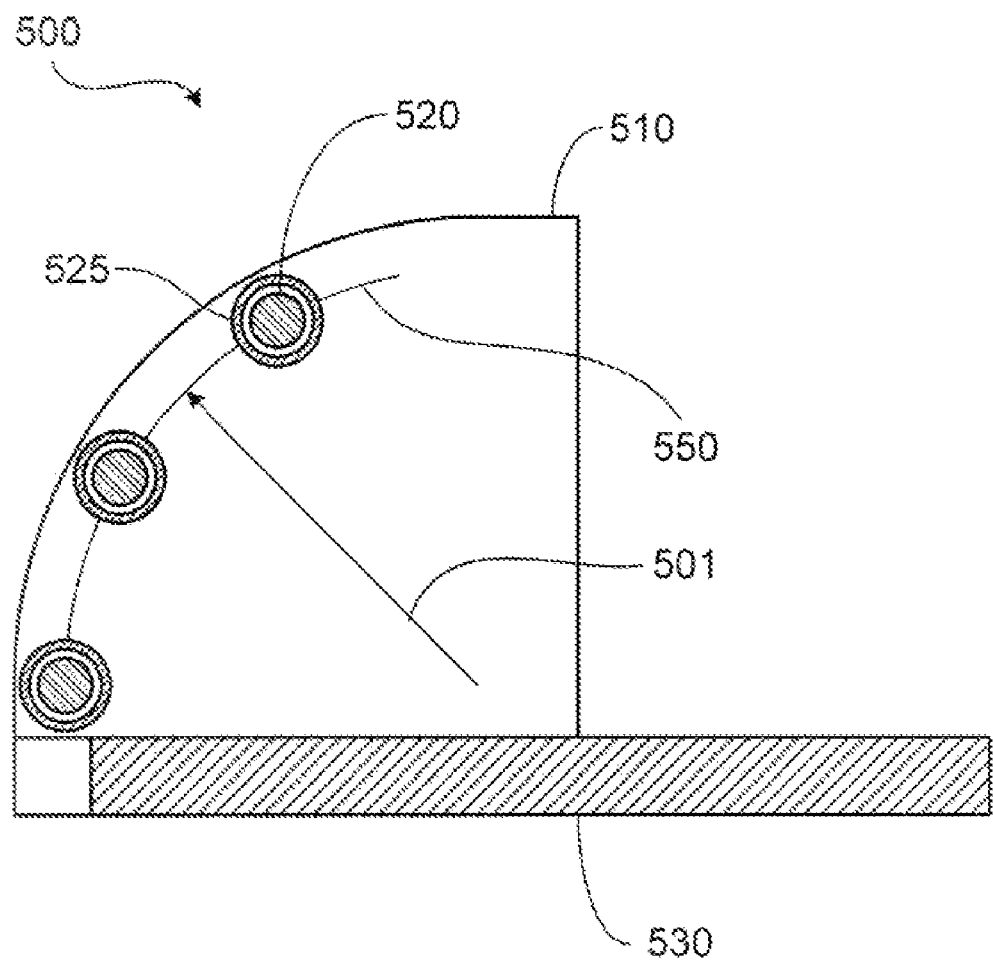
FIG. 5 is a sectional side view of a strain relief tool.

FIG. 5 is a sectional side view of a strain relief tool used in some embodiments of the present invention. In FIG. 5, pin 520 is rotatably supported between end caps 510 and end caps 510 are supported by a mounting bracket 530. Each pin 520 may be supported by placing an end of each pin into a corresponding blind hole in the end caps 510. Each blind hole preferably is sized to allow the pin to rotate freely within the hole. Each pin 520 of the strain relief pin array is shown in FIG. 5 having a sleeve or sheath 525 over each pin. The selection of materials for the end cap 530, pin 520, and sheath 525 for the strain relief tool 500 may use the same criteria described above for the bend tool and preferably use the same corresponding materials for both the bend tool and the strain relief tool. In FIG. 5, the pin axes are disposed along a curve 550 having a constant radius of curvature 501 but it is understood that other curves may be used and are within the scope of the present invention.

Figure 6:
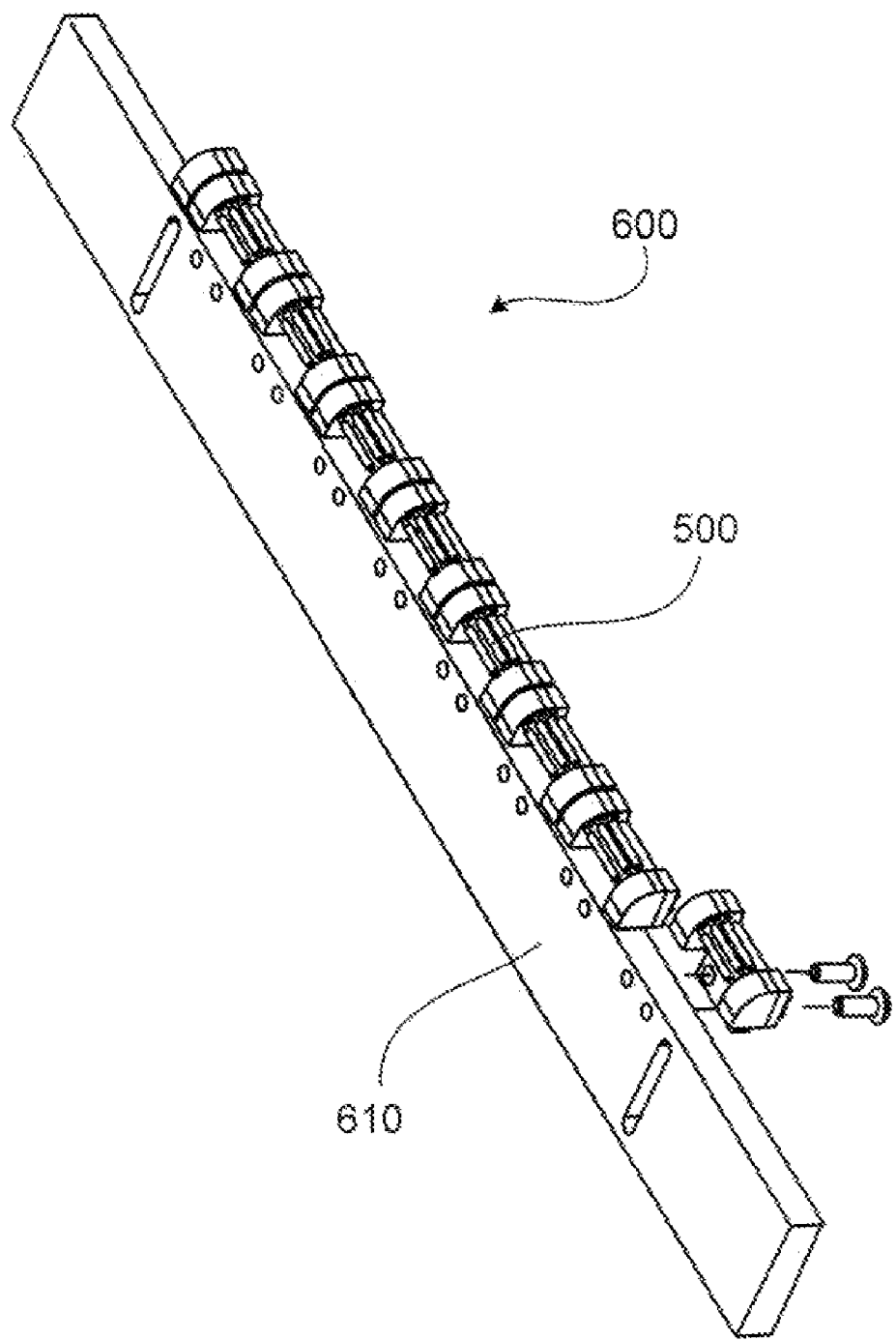
FIG. 6 is a perspective view of a strain relief assembly.

FIG. 6 is a partially exploded perspective view of a strain relief tool assembly 600. The strain relief tool assembly 600 includes at least one strain relief tool 500 mounted on an assembly bracket 610. A strain relief tool assembly 600 may be mounted to, for example, the stationary stage of a fatigue test machine such as that shown in FIG. 1a and provides one of the outer points of the three-point bend configuration. A second strain relief tool assembly 600 may be mounted to the movable stage and provides another of the outer points of the three-point bend configuration. The strain relief tool assemblies enable simultaneous testing of more than one same thereby reducing the time required for testing multiple samples.

Figure 7:
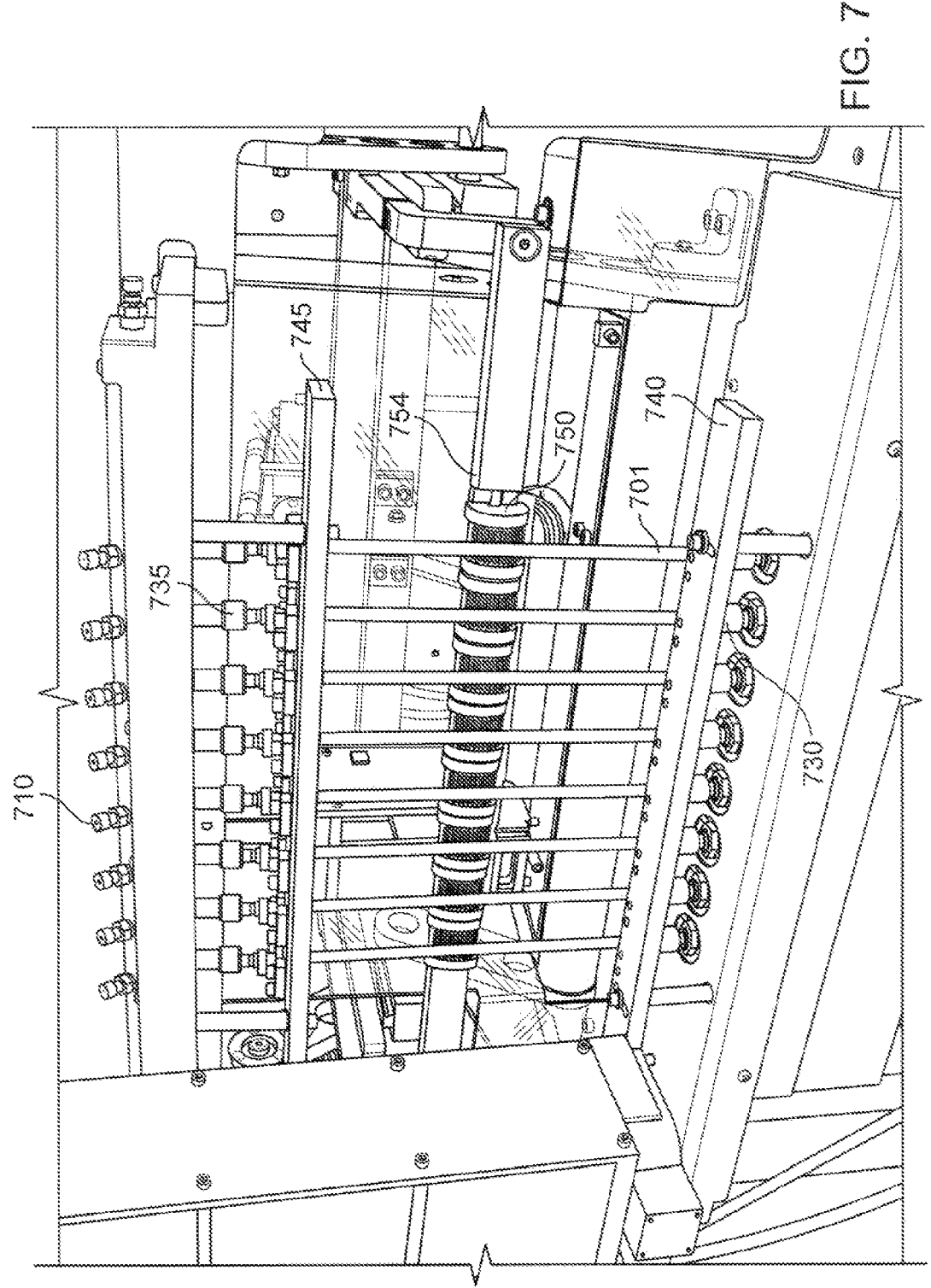
FIG. 7 shows the bend tool assembly of FIG. 4 in a stent fatigue system.

FIG. 7 illustrates a multi-sample fatigue test machine incorporating a bend tool assembly 754 and a strain relief tool assembly 740 and 745. FIG. 7 illustrates a configuration capable of testing up to eight samples, each sample supported by a sample holder 701. Each sample holder 701 is contacted by a corresponding bend tool 750 in the bend tool assembly 754. The two outer points of the three-point bend configuration are provided by an upper strain relief tool assembly 745 and a lower strain relief fool assembly 740. An inlet port 710 enables the user to install the sample stent for testing. An upper sample grip 735 provides support for the sample holder 701 and allows flow to exit the sample holder. A lower sample grip 730 provides support for the sample holder 701 and allows flow to enter the sample holder.

Figure 8:
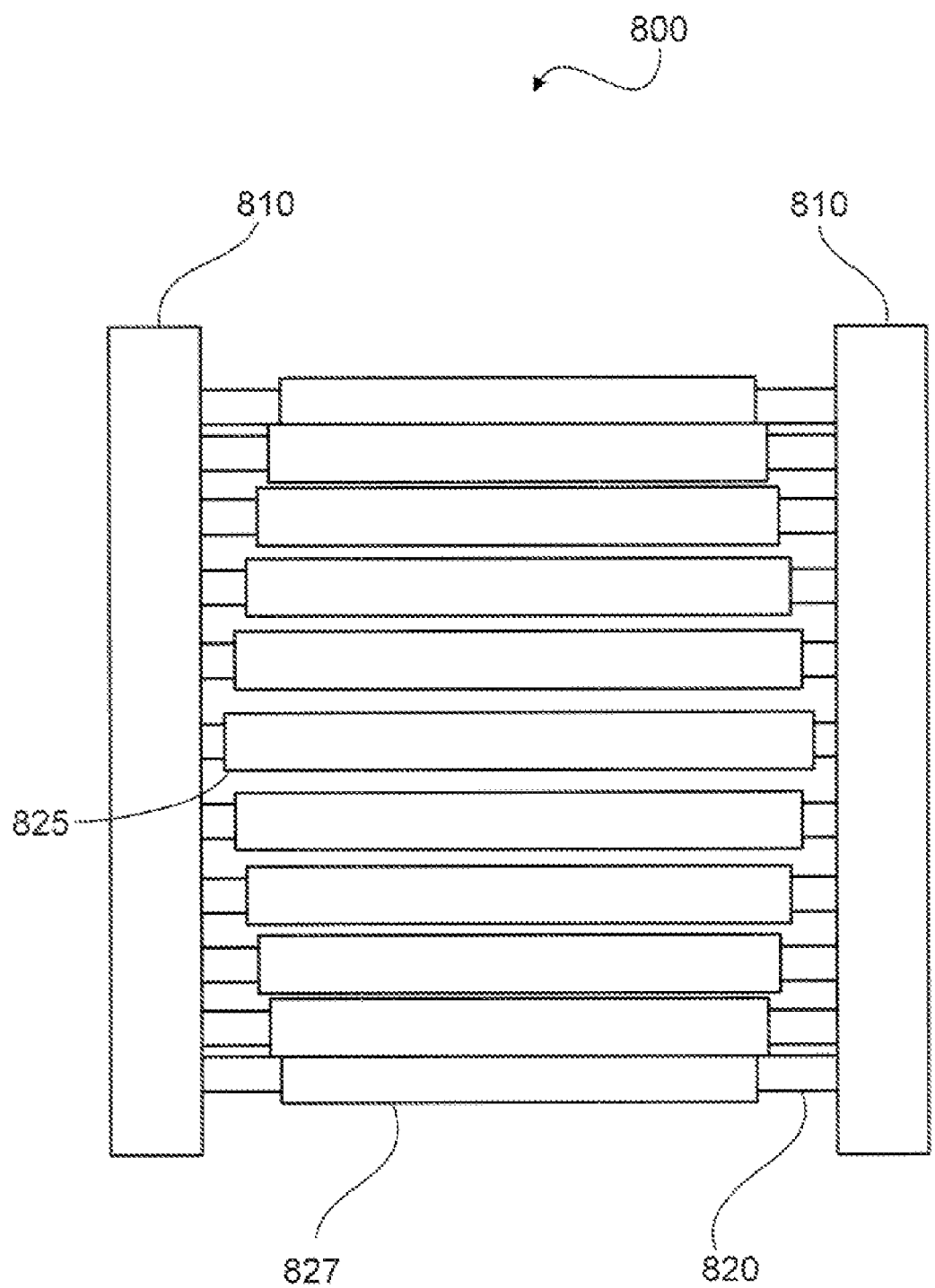
FIG. 8 is front view of another embodiment of a bend tool.

FIG. 8 is a front view of a bend tool 800 that allows the sample holder to be rotated around the longitudinal axis of the sample holder during a bending portion of a fatigue cycle. In FIG. 8, an array of pins is supported at either end by end brackets 810. Each pin 820 in the pin array is partially covered by a sleeve or sheath 827, 825. Each sheath is sized such that the sheath can freely rotate around the corresponding pin and can also slide axially along the pin's longitudinal axis between the end brackets. The selection of materials and sizes of the pin 820, end cap 810, and sheath 827 preferably use the same criteria as the corresponding components of the bend tool shown in FIG. 3. In contrast to FIG. 3, however, sheath length in FIG. 8 varies according to the position of the pin in the pin array. In FIG. 8, sheath 825 covering the center pin in the pin array has the longest length and sheath 827 covering an outer pin in the pin array has the shortest length.

The shorter length sleeves allow for a greater range of axial motion, which may be useful when one or both ends of the sample holder are rotated while being bent. Complicated multi-axis motions such as simultaneous axial strain, bending, and rotation can occur, for example, in the femoral-popliteal artery during walking and it is desirable to test a peripheral artery stent under those expected use conditions. During a combined bend-rotation, the center pin of the bend tool pin array is expected to contact the sample holder first and as the bend tool is laterally displaced to bend the sample holder, the other pins in the pin array make contact progressively from the inner pins to the outer pins in the pin array. If a rotation is applied to the sample holder as the bend tool is bending the sample holder, a tangential shear force on the sample holder may be generated from contact with the pins in the pin array. The contact shear force caused by the rotation of the sample holder may be reduced by allowing the sheath to move along the longitudinal axis of the pin. If the rotation is applied after the bend tool has contacted the sample holder, the outer pins of the pin array may need a larger axial displacement to relieve the contact shear stress on the sample holder and may required a shorter length sleeve than the center pin sleeve.

Having thus described illustrative embodiments of the invention, various modifications and improvements will readily occur to those skilled in the art and are intended to be within the scope of the present invention. For example, although a peripheral artery stent has been used as an illustrative example, other embodiments of the present invention may be applied to coronary artery stents or other implantable devices that experience in-use cyclic strains and are intended to be within the scope of the present invention. Accordingly, the foregoing description is by way of example only and is not intended as limiting. The invention is limited only as defined in the following claims and the equivalents thereto.

What is claimed is:

1. An apparatus comprising:
    a bend tool comprising:
        a first end cap;
        a second end cap; and
        an array of pins, each pin in the array of pins having a first end rotatably supported by the first end cap and a second end rotatably supported by the second end cap, wherein the pins in the array of pins are arranged along a desired bend curve; and
    a sample holder having a tubular structure of elastic material with first and second ends to hold a stent therein and to be bent by contact with the bend tool.

2. The apparatus of claim 1 wherein at least one pin in the pin array supports a rotatable sheath.

3. The apparatus of claim 1 wherein each pin of the pin array supports a rotatable sheath.

4. The apparatus of claim 3 wherein the rotatable sheath slides along a longitudinal axis of the pin between the first and second end cap to reduce a contact sheer force between the rotatable sheath and the sample holder arising from rotation of the sample holder.

5. The apparatus of claim 3 wherein the rotatable sheath is characterized by a length, the sheath length determined by a position of the pin in the pin array wherein a sheath covering an outer pin of the pin array has the shortest length.

6. The apparatus of claim 1 wherein the desired bend curve is characterized by a single radius of curvature.

7. The apparatus of claim 1 wherein the desired bend curve is characterized by a plurality of radii of curvature.

8. The apparatus of claim 1 wherein the desired bend curve simulates an expected in-use bend curve to which the stent is subjected during use within a tubular structure within an organism.

9. The apparatus of claim 1 wherein the apparatus is a fatigue testing device for the stent.

10. The apparatus of claim 1 further comprising a strain relief tool, the strain relief tool having a first relief end cap, a second relief end cap, and an array of relief pins, each relief pin in the array of relief pins having a first end rotatably supported by the first relief end cap and a second end rotatably supported by the second relief end cap.

11. A fatigue testing device for a stent, the device comprising:
    a bend tool, the bend tool including a first end cap, a second end cap, and an array of pins, each pin in the array of pins having a first end rotatably supported by the first end cap and a second end rotatably supported by the second end cap; and
    an upper strain relief tool, the upper strain relief tool having a first relief end cap, a second relief end cap, and an array of relief pins, each relief pin in the array of relief pins having a first end rotatably supported by the first relief end cap and a second end rotatably supported by the second relief end cap.

12. The device of claim 11, wherein at least one pin in the array of pins supports a rotatable sheath able to slide along the longitudinal axis of the at least one pin, and wherein at least one relief pin in the array of relief pins supports another rotatable sheath.

13. The device of claim 12, wherein the rotatable sheath supported by the at least one pin in the array of pins is characterized by a length, the sheath length determined by a position of the pin in the pin array wherein a sheath covering an outer pin of the pin array has the shortest length.

14. The device claim 11, wherein the pins in the array of pins are arranged along a desired bend curve, the desired bend curve simulating an expected in-use bend of the stent, and wherein the relief pins in the array of relief pins are arranged along another desired bend curve.

15. The device of claim 11, further comprising a sample holder having a tubular structure of elastic material with upper and lower ends to hold a stent and to be bent by contact with the bend tool.

16. An apparatus comprising:
    a bend tool comprising:
        a first end cap;
        a second end cap; and
        an array of pins, each pin in the array of pins having a first end held by the first end cap and a second end held by the second end cap, each pin in the array supporting a rotatable sheath, wherein a first pin in the array of pins supports a first sheath characterized by a first length and a second pin in the array of pins supports a second sheath characterized by a second length, the second length different from the first length; and
    a sample holder having a tubular structure of elastic material with first and second ends to hold a stent and to be bent by contact with the bend tool.

17. The apparatus of claim 16 wherein the rotatable sheath is sized to allow rotation of the sheath around a longitudinal axis of the supporting pin and sliding of the sheath along the longitudinal axis of the supporting pin to reduce a contact sheer force between the rotatable sheath and the sample holder arising from rotation of the sample holder.

18. The apparatus of claim 16 wherein the rotatable sheath is characterized by a length, the sheath length determined by a position of the pin in the pin array wherein a sheath covering an outer pin of the pin array has the shortest length.

19. The apparatus of claim 16 wherein the pins in the array of pins are arranged along a desired bend curve, the desired bend curve simulating an expected in-use bend of the stent during use within a tubular structure within an organism.

20. The apparatus of claim 16 further comprising a strain relief tool, the strain relief tool having a first relief end cap, a second relief end cap, and an array of relief pins, each relief pin in the array of relief pins having a first end rotatably supported by the first relief end cap and a second end rotatably supported by the second relief end cap.

* * * * *